United States Patent [19]

Macholdt et al.

[11] Patent Number: 5,342,723
[45] Date of Patent: Aug. 30, 1994

[54] BISCATIONIC ACID AMIDE AND ACID IMIDE DERIVATIVES AS CHARGE CONTROLLERS

[75] Inventors: Hans-Tobias Macholdt, Darmstadt; Siegfried Schiebler, Bad Soden am Taunus; Jörg Gitzel, Hattersheim am Main; Erwin Dietz, Kelkheim/Taunus, all of Fed. Rep. of Germany

[73] Assignee: Hoechst Aktiengesellschaft, Frankfurt, Fed. Rep. of Germany

[21] Appl. No.: 863,296

[22] PCT Filed: Dec. 17, 1990

[86] PCT No.: PCT/EP90/02207

§ 371 Date: Jun. 25, 1992

§ 102(e) Date: Jun. 25, 1992

[87] PCT Pub. No.: WO91/10172

PCT Pub. Date: Jul. 11, 1991

[30] Foreign Application Priority Data

Dec. 28, 1989 [DE] Fed. Rep. of Germany ....... 3943048
Sep. 5, 1990 [DE] Fed. Rep. of Germany ....... 4028122

[51] Int. Cl.$^5$ .......................... G03C 9/08; C07F 5/06; C07F 7/02; C07F 11/00
[52] U.S. Cl. ........................................ 430/110; 546/8; 544/225; 548/404

[58] Field of Search .............................. 430/110; 546/8; 544/225; 548/404

[56] References Cited

U.S. PATENT DOCUMENTS

| | | | |
|---|---|---|---|
| 3,893,939 | 7/1975 | De Kalb et al. | 252/301.4 P |
| 4,057,426 | 11/1977 | Mammino et al. | 96/1 SD |
| 4,415,646 | 11/1983 | Gruber et al. | 430/110 |
| 4,493,883 | 1/1985 | Gruber et al. | 430/110 |
| 4,496,643 | 1/1985 | Wilson et al. | 430/110 |
| 4,656,112 | 4/1987 | Kawagishi et al. | 430/110 |
| 4,683,188 | 7/1987 | Suzuki et al. | 430/110 |
| 4,684,596 | 8/1987 | Bonser et al. | 430/110 |
| 4,927,729 | 3/1990 | Harnisch et al. | 430/110 |

*Primary Examiner*—Marion E. McCamish
*Assistant Examiner*—Mark A. Chapman
*Attorney, Agent, or Firm*—Connolly and Hutz

[57] ABSTRACT

Use of biscationic acid imide and acid imide derivatives whose anion is the stoichiometric equivalent of one or more organic or inorganic, mixed or non-mixed anions, the compounds also being able to exist as mixed crystals with different cations, individually or in combination, as charge controllers for toners and developers employed for electrophotographic copying or multicopying of originals and for printing electronically, optically or magnetically stored data or in color proofing, and as charge controllers for powders and powder paints.

10 Claims, No Drawings

BISCATIONIC ACID AMIDE AND ACID IMIDE DERIVATIVES AS CHARGE CONTROLLERS

The present invention relates to the use of biscationic acid amide derivatives and acid imide derivatives as colorless charge controllers in toners and developers for electrophotographic recording processes. Due to the controlled chemical linkage of specific acid amide groupings or acid imide groupings with two components in each case containing ammonium or phosphonium, combination of these units taking place via the particular amide nitrogens or imide nitrogens, the compounds according to the invention have particularly high and constant charge control properties, excellent heat stabilities and a very good dispersibility.

In electrophotographic recording processes, a "latent charge image" is generated on a photoconductor. This is effected, for example, by charging of a photoconductor by a corona discharge and subsequent imagewise exposure to light of the electrostatically charged surface of the photoconductor, the exposure to light causing the charge to drain to the earthed substrate at the exposed points. The "latent charge image" thus produced is then developed by application of a toner. In a subsequent step, the toner is transferred from the photoconductor to, for example, paper, textiles, films or plastic, and is fixed there, for example by pressure, radiation, heat or the action of solvents. The used photoconductor is then cleaned and is available for a new recording operation.

The optimization of toners is described in numerous patent specifications, the influence of the toner binder (variation of resin/resin components or wax/wax components), the influence of controllers or other additives or the influence of carriers (in two-component developers) and magnetic pigments (in one-component developers), inter alia, being investigated.

A measure of the toner quality is its specific charge q/m (charge per unit measure). In addition to the symbol and level of the electrostatic charge, a critical quality criterion is that the desired charge level is achieved rapidly and that this charge remains constant over a relatively long activation period. In practice, this is of central importance inasmuch as the toner may be exposed to a considerable activation time in the developer mixture before it is transferred to the photoconductor, since it sometimes remains in the developer mixture for a period for production of up to several thousand copies. The insensitivity of the toner to climatic influences, such as temperature and atmospheric humidity, is moreover another important suitability criterion.

Both positively and negatively chargeable toners are used in copiers and laser printers, depending on the type of process and apparatus.

So-called charge controllers (also called charge control agents) are often added in order to obtain electrophotographic toners or developers with either positive or negative triboelectric charging. In addition to the symbol of the charge control, the extent of the controlling effect is of importance, since a higher activity allows a small amount to be used.

Since toner binders by themselves as a rule show a marked dependence of the charging on the activation time, the object of a charge controller is on the one hand to establish the sign and level of the toner charge and on the other hand to counteract the charge drift of the toner binder and ensure a constant toner charge. Charge controllers which cannot prevent the toner or developer from displaying a high charge drift over a prolonged use period (ageing), and which can even cause the toner or developer to undergo a charge reversal, are therefore unsuitable in practice.

Full color copiers and laser printers operate by the trichromism principle, which necessitates exact matching of the color shades of the three primary colors (yellow, cyan and magenta). The slightest shifts in color shade even of only one of the three primary colors necessarily require a shift in color shade of the other two colors so that full color copies and prints which are true to the original can also then be produced.

Because of this precise matching of the coloristic properties of the individual coloring agents to one another which is required in these color toners, charge controllers with absolutely no intrinsic color are especially important.

In the case of color toners, the three toners of yellow, cyan and magenta must also be matched to one another exactly in respect of their triboelectric properties, as well as meeting precisely defined color-related requirements. This triboelectric matching is necessary, because the three color toners (or four color toners, if black is also included) must be transferred in succession in the same apparatus for a full color print or full color copy.

It is known that in some cases color agents can very adversely influence the triboelectric charging of toners (H.-T. Macholdt, A. Sieber, Dyes & Pigments 9 (1988), 119-27, U.S. Pat. No. 4,057,426). Because of the different triboelectric effects of coloring agents and the resulting, in some cases very pronounced, influence on toner chargeability, it is not possible to add them as the exclusive coloring agent in a toner base recipe compiled once and for all. Rather, it may be necessary to establish an individual recipe for each coloring agent, for which, for example, the nature and amount of charge controller required are tailor-made specifically. This procedure is correspondingly involved and additionally adds to the difficulties already described in color toners for process color (trichromism).

Highly active colorless charge controllers which are capable of compensating the different triboelectric properties of various coloring agents and of imparting the desired charge to the toner are therefore required. In this manner, coloring agents which have very different triboelectric properties can be employed in the various toners required (yellow, cyan, magenta and if appropriate black) with the aid of a toner base recipe compiled once and for all using one and the same charge controller. It is moreover important in practice for the charge controller to have a high heat stability and good dispersibility. Typical temperatures for incorporating charge controllers into the toner resins are between 100° C. and 200° C. if, for example, kneaders or extruders are used. A heat stability of 200° C., and preferably even 250° C., is accordingly a great advantage. It is also important for the heat stability to be ensured over a prolonged period of time (about 30 minutes) and in various binder systems. Typical toner binders are polymerization, polyaddition and polycondensation resins, such as, for example, styrene resins, styrene acrylate styrene butadiene resins, acrylate resins, polyester resins, amide resins, amine resins, ammonium resins, ethylene resins, phenolic resins and epoxy resins, individually or in coordination, which can also contain other constituents, or to which other constituents can be added subsequently, such as coloring agents, waxes or flow auxiliaries.

This is important, since constantly occurring matrix effects lead to premature decomposition of the charge controller in the toner resin, which means that the toner resin becomes dark yellow or dark brown in color and the charge control effect is completely or partly lost.

For a good dispersibility it is of great advantage if the charge controller as far as possible has no wax-like properties, no tackiness and a melting or softening point of >150° C., and preferably >200° C. Tackiness often leads to problems during metering into the toner formulation, and low melting or softening points can mean that no homogeneous distribution is achieved when the substance is dispersed in, since the material combines, for example in droplet form, in the carrier material.

Colorless charge controllers are claimed in numerous patent specifications. Thus, for example, DE-OS 3144017, U.S. Pat. No. 4,656,112 and JP-OS 61-236557 describe metal complexes and metal organyls, DE-OS 3837345, DE-OS 3738948, DE-OS 3604827, EP-OS 242420, EP-OS 203532, U.S. Pat. Nos. 4,684,596, 4,683,188 and 4,493,883 describe ammonium and immonium compounds and DE-OS 3912396, U.S. Pat. Nos. 3,893,939 and 4,496,643 describe phosphonium compounds as colorless charge controllers for electrophotographic toners.

Nevertheless, the colorless charge controllers known to date have a number of disadvantages which severely limit or sometimes render impossible their use in practice. The chromium, iron, cobalt and zinc complexes described in DE-OS 3144017 and U.S. Pat. No. 4,656,112 and the antimony organyls described in JP-OS 61-236557 thus also have, in addition to the problems of heavy metals, the disadvantage that in some cases they are not actually colorless, and therefore are of only limited use in color toners.

The known quaternary ammonium compounds, which are suitable per se, are often difficult to disperse, which leads to non-uniform charging of the toner. In addition, the problem often arises that the toner charge generated by these compounds is not stable over a prolonged activation period (up to 24 hours activation time), especially at a high temperature and atmospheric humidity (EP-OS 242420), which then leads to a build-up of incorrectly or inadequately charged toner particles in the course of a copying or printing process and hence brings the process to a standstill. It is furthermore known that ammonium- and immonium-based charge controllers are sensitive to light or mechanical effects (EP-OS 203532 and U.S. Pat. No. 4,683,188) and can be unstable to heat, and that they form decomposition products which may have an adverse effect on triboelectric charging of the toner (U.S. Pat. No. 4,684,596) and/or have a deep, often dark brown, intrinsic color (DE-OS 3738948, DE-OS 3604827 and U.S. Pat. No. 4,493,883). Moreover, they often display wax-like properties, in some cases water-solubility and/or a low activity as charge controllers.

Charge controllers which are suitable per se and are based on highly fluorinated ammonium, immonium and phosphonium compounds (DE-OS 3912396 and DE-OS 3837345) have the disadvantage of an involved synthesis, which results in high preparation costs for the corresponding substances, and they are not sufficiently stable to heat. Phosphonium salts are less active as charge controllers than ammonium salts (U.S. Pat. Nos. 3,893,939 and 4,496,643) and may cause toxicological problems.

As well as being used in electrophotographic toners and developers, charge controllers can also be employed to improve triboelectric charging of powders and paints, in particular in triboelectrically or electrokinetically sprayed powder paints, such as are used for surface coating of objects of, for example, metal, wood, plastic, glass, ceramic, concrete, textile material, paper or rubber.

Powder paint technology is used, inter alia, for painting small objects, such as garden furniture, camping articles, domestic appliances, small components for vehicles, refrigerators and shelving, and for painting workpieces of complicated shape. The powder paint or powder in general contains its electrostatic charge by one of the following two processes:

a) In the corona process, the powder paint or powder is passed over a charged corona and becomes charged during this operation.

b) In the triboelectric or electrokinetic process, the principle of frictional electricity is used. The powder paint or powder is given, in the spray apparatus, an electrostatic charge which is opposite to the charge of the friction partner, in general a flexible hose or spray pipe (for example of polytetrafluoroethylene).

A combination of the two processes is also possible. The powder paint resins employed are, typically, epoxy resins, polyester resins containing carboxyl and hydroxyl groups and acrylic resins, together with the corresponding curing agents. Combinations of resins are also used. Thus, for example, epoxy resins are often employed in combination with polyester resins containing carboxyl and hydroxyl groups.

Typical curing agent components for epoxy resins are, for example, acid anhydrides, imidazoles and dicyandiamide and derivatives thereof. Typical curing agent components for polyester resins containing hydroxyl groups are, for example, acid anhydrides, masked isocyanates, bisacylurethanes, phenolic resins and melamine resins, and typical curing agent components for polyester resins containing carboxyl groups are, for example, triglycidyl isocyanurates or epoxy resins. Typical curing agent components which are used in acrylic resins are, for example, oxazolines, isocyanates, triglycidyl isocyanurates or dicarboxylic acid as the curing agent component.

The lack of an inadequate charge is to be observed, above all, in triboelectrically or electrokinetically sprayed powders and powder paints which have been prepared on the basis of polyester resins, in particular polyesters containing carboxyl groups, or on the basis of so-called mixed powders, also called hybrid powders. Mixed powders are understood as meaning powder paints, the resin base of which consists of a combination of epoxy resin and polyester resin containing carboxyl groups. Mixed powders form the basis of the powder paints represented most often in practice.

The aim of the present invention was therefore to discover improved, particular active colorless charge controllers with which, in addition to the charge level, rapid achievement and constancy of this charge had to be ensured, and with which the charge effect should not be sensitive to changes in temperature and atmospheric humidity. These compounds moreover had to be highly heat-stable, above all also over a prolonged period of time in the particular carrier material (resin), and waterinsoluble, readily dispersible and compatible with the toner contents. Moreover, the synthesis of the compounds should not be very complex and their preparation should be inexpensive.

Surprisingly, it has now been found that specific biscationic acid amide derivatives and acid imide derivatives are particularly active charge controllers for electrophotographic toners and developers, and moreover can also be employed as charge-improving agents in powders and paints for surface coating, in particular electrokinetically sprayed powder paints.

Because of their colorlessness, high activity, good compatibility and dispersibility in customary toner resins and chemical inertness, and because of the insensitivity of the charge controlling effect to variation in temperature and atmospheric humidity, the compounds are particularly suitable for use in color toners or developers for full color copiers and full color laser printers operating by the trichromism principle (substractive color mixing), and also for colored toners or developers in general and for black toners or developers. The compounds are furthermore also suitable for coating carriers.

A great technical advantage of these readily dispersible compounds lies in the fact that substances of the same class of compounds can be employed either as positive or as negative controllers, depending on the cation/anion combination. Problems during incorporation into the toner binder and of compatibility with the toner binder after a toner base recipe has been compiled are thus minimized.

Either positive or negative toners can thus be prepared from a solid toner base recipe (consisting of toner binders, coloring agent, flow auxiliary and if appropriate other components) by incorporating in the desired controller.

It is particularly advantageous that the synthesis of the compounds claimed according to the invention is not particularly involved and their preparation is very inexpensive.

The present invention thus relates to the use of biscationic acid amide derivatives and acid imide derivatives of the general formula (I) and/or (II) and/or (III)

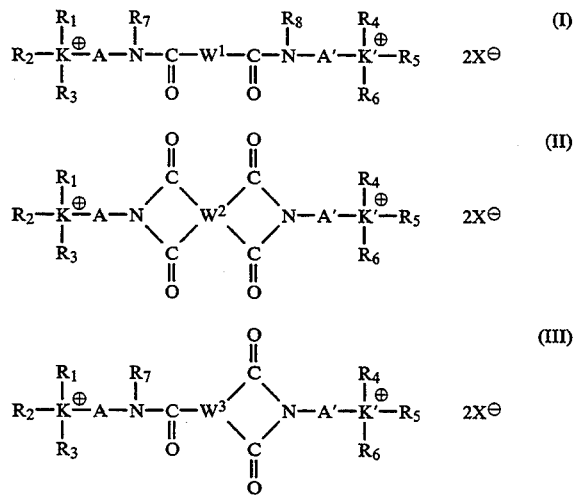

in which $R_1$ to $R_8$ independently of one another are a hydrogen atom, a hydrocarbon radical, which can be interrupted by hetero atoms, such as, for example, straight-chain or branched, saturated or unsaturated alkyl groups having 1 to 30 carbon atoms, preferably 1 to 22 carbon atoms, polyoxyalkylene groups, preferably polyoxyethylene or polyoxypropylene groups, of the general formula -(alkylene-O)n-R, in which R is an H atom or an alkyl($C_1$–$C_4$) group or acyl group, such as, for example, the acetyl, benzoyl, or naphthoyl group, and n is a number from 1 to 10, preferably 1 to 4, mono- or polynuclear cycloaliphatic radicals having 5 to 12 carbon atoms, such as, for example, cyclohexyl or cyclopentyl groups, mono- or polynuclear aromatic radicals, such as, for example, phenyl, naphthyl, tolyl, or biphenyl radicals, or araliphatic radicals, such as, for example, the benzyl radical, in which the aliphatic, cycloaliphatic, araliphatic and aromatic radicals can be substituted by acid groups, preferably carboxylic acid and/or sulfonic acid groups, or salts, amides or esters thereof, alkyl($C_1$–$C_4$), hydroxyl or alkoxy($C_1$–$C_4$) groups or primary, secondary or tertiary amino groups, such as, for example, N-monoalkyl($C_1$–$C_4$)amino or N-dialkyl ($C_1$–$C_4$)-amino groups, and by fluorine, chlorine or bromine atoms, the aliphatic radicals preferably by 1 to 45 fluorine atoms, and in which the aliphatic, cycloaliphatic, araliphatic or aromatic ring systems can contain one or more hetero atoms, such as, for example, nitrogen and/or oxygen and/or sulfur and/or phosphorus atoms, and in which, independently of one another, $R_1$ and $R_2$ together with K, or $R_4$ and $R_5$ together with K' can be closed to form a saturated or unsaturated, preferably aromatic ring system having 5 to 7 atoms, which can contain further hetero atoms, preferably nitrogen and/or oxygen and/or sulfur atoms, and in which the particular ring system can in turn be substituted and/or modified by condensation on or bridging to further ring systems, and in which, in the case where $R_1$ or $R_2$, or $R_4$ or $R_5$ form a double bond to K or K', $R_3$ or $R_6$ has no meaning, are, and/or one of the radicals $R_1$, $R_2$ or $R_3$ can close together with $R_7$, or one of the radicals $R_4$, $R_5$ or $R_6$ can close together with $R_8$ to form an aliphatic bridge of 2 to 5 carbon atoms, and in which A and A' are organic bridge members, and preferably independently of one another are straight-chain or branched, saturated or unsaturated alkylene men, pets having 1 to 30 carbon atoms, preferably 1 to 12 carbon atoms, mono- or polynuclear cycloaliphatic members, such as, for example, cyclohexylene or cyclopentylene, mono- or polynuclear aromatic members, such as, for example, phenylene, naphthylene, tolylene or biphenylene, or araliphatic members, such as, for example, benzylene, xylylene, mesitylene, benzoylene or benzoyleneamide, in which the aliphatic, cycloaliphatic, araliphatic and aromatic members can be substituted by acid groups, preferably carboxylic acids and/or sulfonic acid groups, or salts or amides thereof, alkyl($C_1C_4$), hydroxyl or alkoxy($C_1$–$C_4$) groups or primary, secondary or tertiary amino groups, such as, for example, N-monoalkyl($C_1$–$C_4$)amino or N-dialkyl($C_1$–$C_4$)amino groups, and by fluorine, chlorine or bromine atoms, and the aliphatic members preferably by 1 to 45 fluorine atoms, and in which the aliphatic, aromatic and araliphatic ring systems can contain one or more hetero atoms, such as, for example, nitrogen and/or oxygen and/or sulfur and/or phosphorus atoms, and in which $W^1$, $W^2$ and $W^3$ independently of one another represents an organic bridge member, such as, for example, a straight-chain or branched, saturated or unsaturated aliphatic bridge member having 1 to 30 carbon atoms, preferably 1 to 22 carbon atoms, a polyoxyalkylene member, preferably a polyoxyethylene or polyoxypropylene member, of the general formula —CH$_2$—O—(alkylene[C$_1$-C$_5$]—O)—m—CH$_2$—, in which m is a number from 0 to 10, preferably from 1 to 4, a mono- or polynuclear cycloaliphatic bridge member having 5 to 12 carbon atoms, such as, for example, cyclopentylene or cyclohexylene, a mono- or polynuclear aromatic bridge member, such as, for example, phenylene, naphthylene, tolylene or biphenylene, or an araliphatic bridge member, such as, for example, benzylene, in which the aliphatic, cycloaliphatic, araliphatic and aromatic members can be substituted by acid groups, preferably carboxylic acids and/or sulfonic acid groups or salts, amides or esters thereof, hydroxyl, alkyl(C$_1$-C$_4$) or alkoxy(C$_1$-C$_4$) groups or primary, secondary or tertiary amino groups, such as, for example, N-monoalkyl(C$_1$-C$_4$)amino or N-dialkylamino(C$_1$-C$_4$) groups, and by fluorine, chlorine or bromine atoms, and the aliphatic members preferably by 1 to 45 fluorine atoms, and in which the aliphatic intermediate members and the cycloaliphatic, the araliphatic and the aromatic ring systems can contain one or more hetero atoms, such as, for example, nitrogen and/or oxygen and/or sulfur and/or phosphorus atoms, and in which W$^1$ is a divalent, W$^2$ a tetravalent and W$^3$ a trivalent intermediate member, and in which W$^1$, in the case of the general formula (I), can also be a direct bond, and K and K' independently of one another is a nitrogen, phosphorus, arsenic or antimony, preferably a nitrogen atom, and the anion X$^\ominus$ is the stoichiometric equivalent of one or more mixed or non-mixed anions, it being possible for the compound also to be present as a mixed crystal with various cations of the general formula (I) to (III), individually or in combination as charge controllers in electrophotographic toners and developers which are employed for electrophotographic copying or multicopying of originals and for printing electronically, optically or magnetically stored data or in color proofing.

The compounds claimed according to the invention are moreover suitable as charge controllers in powders and paints for surface coating of objects of metal, wood, plastic, glass, ceramic, concrete, textile material, paper or rubber, in particular in triboelectrically or electrokinetically sprayed powder paints. The compounds claimed according to the invention are present in an amount of about 0.01 to about 30 percent by weight, preferably 0.1 to about 5 percent by weight, as a homogeneous distribution in the particular toner, developer, paint or powder. These compounds can moreover also be incorporated as charge-improving agents into the coating of carriers which are employed in developers of electrophotographic copiers or printers.

Compounds which are particularly suitable are those in which K and K' are nitrogen, R$_1$ to R$_6$ independently of one another are H atoms or straight-chain or branched alkyl groups (C$_1$-C$_6$), such as, for example, methyl, ethyl, n-propyl, iso-propyl, tertiary butyl, pentyl and/or hexyl, and those in which, independently of one another, R$_1$ and R$_2$, or R$_4$ and R$_5$, incorporating K or K', can be closed together to form a saturated or unsaturated, heterocyclic ring system having one or more nitrogen atoms as the hereto atom, such as, for example, pyrrole, pyrroline, pyrrolidine, pyrazole, pyrazolone, pyrazoline, hexamethyleneimine, imidazole, oxazole, thiazole, triazole, pyridine, piperidine, pyrazine, piperazine, pyrimidine or morpholine, in which these ring systems can in turn be substituted, preferably by straight-chain alkyl(C$_1$-C$_4$) groups, or can be enlarged by condensation or bridging to ring systems such as quinoline, indole, indoline, purine, quinoxaline, benzothiazole, acridine, benzoquinoline, carbazole, benzophenazine, phenanthroline, bipiperidine, bipyridine, phenazine, benzacridine or nicotine, and in which R$_3$ and/or R$_6$ are a hydrogen atom or an alkyl(C$_1$-C$_4$) group, and in which R$_3$ and/or R$_6$ can also be omitted completely if there is a double bond between K or K' and an adjacent atom in the ring system formed by incorporation of K or K', R$_7$ and R$_8$ are a hydrogen atom, and A and A' independently of one another is a —CH=C(COOH)—CH$_2$—, —CH$_2$—(CH$_2$—CH=CH—)n or —(CH$_2$—)n bridge member where n is 1 to 12, preferably 1 to 4, or a phenylene, naphthylene or

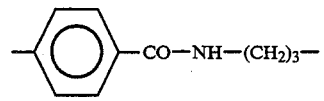

bridge member, W$^1$ [lacuna] a phenylene, naphthylene, cyclohexylene, (CH$_2$)q, where q is 1 to 12, or a (CH$_2$—O(CH$_2$—CH$_2$-O),—CH$_2$—bridge member, where r is 1 to 4, W$^2$ is a phenylene or naphthylene bridge member, in which the carboxyl groups required for imide formation are in each case in the ortho-position relative to one another in the case of phenylene and in the ortho- and/or periposition relative to one another in the case of naphthylene, or an ethylenediaminetetramethylene bridge member and W$^3$ is a phenylene or naphthylene bridge member, in which at least two carboxyl groups participating in the imide bond are in the ortho- or peri-position relative to one another, and the third carboxyl group can be in any desired position relative to these, and in which, in the case where A, A' and W$^1$, the phenylene bridge members are bridged to the particular K or K' on the one side and to the imide or amide nitrogen on the other side or substituted by the particular carbonyl functions in the 1,2; 1,3; or 1,4-position, preferably in the 1,3 and 1,4-position, the naphthylene bridge members in the 1,2 to 1,8 and in the 2,3 to 2,8 position and the cyclohexylene bridge members in the 1,2; 1,3; or 1,4-position, preferably in the 1,3 or 1,4-position, and the anion X$^\ominus$ is the equivalent or equivalents of a corresponding organic or inorganic anion, in the case of monovalent inorganic anions, for example BF$_4^\ominus$, B(aryl)$_4^\ominus$, such as, for example, tetraphenylborate, chlorotetraphenylborate, methyltetraphenylborate, tetranaphthylborate, tetrafluorophenylborate, tetramethoxyphenylborate, tetrabiphenylborate, tetrabenzylborate or tetrapyridylborate, PF$_6^\ominus$, SCN$^\ominus$, HSO$_4^\ominus$, F$^\ominus$, Cl$^\ominus$, Br$^\ominus$, I$^\ominus$, CN$^\ominus$, ClO$_4^\ominus$, sulfate, hydrogen sulfate, zinc tetracyanate, zinc tetrathiocyanate, tungstate, molybdate, phosphomolybdate and -tungstate and silicomolybdate- and tungstate, and of organic anions, for example ethyl- and methyl-sulfate, saturated or unsaturated aliphatic or aromatic carboxylate or sulfonate, such as, for example, acetate, lactate, oxalate benzoate, salicylate, 2-hydroxy-3-naphthoate, 2-hydroxy-6-naphthoate, ethylsulfonate, phenylsulfonate, 4-toluenesulfonate or 4-aminotoluene-3-sulfonate, and furthermore perfluorinated, saturated or unsaturated, aliphatic or aromatic carboxylate or sulfonate, such as, for example, perfluoroacetate, perfluoroalkylbenzoate, perfluoroethylsulfonate or perfluoroalkyl-benzenesulfonate, and saturated and unsaturated aliphatic or aromatic di- or tricarboxylic acid or di- and trisulfonic acid anions, are the anions BF$_4^\ominus$, B(aryl)$_4^\ominus$, PF$_6^\ominus$, SCN$^\ominus$, CH$_3$SO$_4^\ominus$, C$_2$H$_5$SO$_4^\ominus$, HSO$_4^\ominus$ and P[Mo$_3$O$_{10}$]$_4^{3\ominus}$ being particularly suitable.

Examples of individual compounds which may be mentioned are:

| Compound | Cation | Anion |
|---|---|---|
| 1.1a | ![structure with H₃C—N⊕(CH₃)(CH₃)—(CH₂)₃—N(H)—C(O)—C₆H₄—C(O)—N(H)—(CH₂)₃—N⊕(CH₃)(CH₃)—CH₃] | 2 × BF₄⊖ |
| 1.1b | ″ | 2 × PF₆⊖ |
| 1.1c | ″ | 2 × B(C₆H₅)₄⊖ |
| 1.1d | ″ | 2 × SCN⊖ |
| 1.1e | ″ | 2 × CH₃SO₄⊖ |
| 1.2a | ![structure with CH₃/CH₃/H on N⊕, (CH₂)₃, amide, phenylene, amide, (CH₂)₃, N⊕(CH₃)(CH₃)(H)] | 2 × BF₄⊖ |
| 1.2b | ″ | 2 × PF₆⊖ |
| 1.2c | ″ | 2 × B(C₆H₅)₄⊖ |
| 1.2d | ″ | 2 × SCN⊖ |
| 1.2e | ″ | 2 × CH₃SO₄⊖ |
| 1.3a | ![structure with C₂H₅/CH₃ on N⊕, (CH₂)₃, amide, phenylene, amide, (CH₂)₃, N⊕(CH₃)(C₂H₅)(C₂H₅)] | 2 × BF₄⊖ |
| 1.3b | ″ | 2 × B(C₆H₅)₄⊖ |

-continued

| Compound | Cation | Anion |
|---|---|---|
| 1.4a | ![structure] bis-amide with -(CH2)7-N+(CH3)3 groups | 2 × BF4⁻ |
| 1.4b | " | 2 × B(C6H5)4⁻ |
| 1.5a | bis-amide with -(CH2)10-N+(CH3)3 groups | 2 × BF4⁻ |
| 1.5b | " | 2 × B(C6H5)4⁻ |
| 1.6a | bis-amide with -(CH2)3-N+(imidazole-CH3) groups | 2 × BF4⁻ |
| 1.6b | " | 2 × B(C6H5)4⁻ |
| 1.7a | bis-amide with -(CH2)3-N+(piperidine-CH3) groups | 2 × BF4⁻ |
| 1.7b | " | 2 × B(C6H5)4⁻ |

-continued

| Compound | Cation | Anion |
|---|---|---|
| 1.8a | morpholine-N⁺(CH₃)-(CH₂)₃-NH-CO-C₆H₄-CO-NH-(CH₂)₃-N⁺(CH₃)-morpholine | 2 × BF₄⁻ |
| 1.8b | " | 2 × B(C₆H₅)₄⁻ |
| 1.9a | (CH₃)₃N⁺-(CH₂)₃-NH-CO-C₆H₄-CO-NH-(CH₂)₃-N⁺(CH₃)₃ | 2 × BF₄⁻ |
| 1.9b | " | 2 × B(C₆H₅)₄⁻ |
| 1.10a | (C₂H₅)₃N⁺-(CH₂)₃-NH-CO-C₆H₄-CO-NH-(CH₂)₃-N⁺(C₂H₅)₃ | 2 × BF₄⁻ |
| 1.10b | " | 2 × B(C₆H₅)₄⁻ |
| 1.11a | H-N⁺(C₂H₅)₂-(CH₂)₃-NH-CO-C₆H₄-CO-NH-(CH₂)₃-N⁺(C₂H₅)₂-H | 2 × PF₆⁻ |
| 1.11b | " | 2 × BF₄⁻ |
| 1.11c | " | 2 × B(C₆H₅)₄⁻ |

-continued

| Compound | Cation | Anion |
|---|---|---|
| 1.11d | " | 2 × SCN⁻ |
| 1.11e | " | 2 × CH₃SO₄⁻ |
| 2.1a | (3-disubstituted benzene with two –C(=O)–NH–(CH₂)₃–N⁺(CH₃)₃ groups) | 2 × BF₄⁻ |
| 2.1b | " | 2 × B(C₆H₅)₄⁻ |
| 3.1a | cis/trans 1,4-cyclohexane with two –C(=O)–NH–(CH₂)₃–N⁺(CH₃)₃ groups | 2 × BF₄⁻ |
| 3.1b | " | 2 × PF₆⁻ |
| 3.1c | " | 2 × B(C₆H₅)₄⁻ |
| 3.1d | " | 2 × SCN⁻ |
| 3.1e | " | 2 × CH₃SO₄⁻ |
| 3.2a | cis/trans 1,4-cyclohexane with two –C(=O)–NH–(CH₂)₃–N⁺H(CH₃)₂ groups | 2 × BF₄⁻ |
| 3.2b | " | 2 × PF₆⁻ |
| 3.2c | " | 2 × B(C₆H₅)₄⁻ |

-continued

| Compound | Cation | Anion |
|---|---|---|
| 3.2d | | 2 × SCN⊖ |
| 3.2e | | 2 × CH₃SO₄⊖ |
| 3.3a | cis/trans H₅C₂—⊕N(CH₃)₂—(CH₂)₇—NH—C(=O)—[cyclohexane-H]—C(=O)—NH—(CH₂)₃—⊕N(CH₃)₂—C₂H₅ | 2 × BF₄⊖ |
| 3.3b | " | 2 × B(C₆H₅)₄⊖ |
| 3.4a | cis/trans H₃C—⊕N(CH₃)₂—(CH₂)₇—NH—C(=O)—[cyclohexane-H]—C(=O)—NH—(CH₂)₂—⊕N(CH₃)₂—CH₃ | 2 × BF₄⊖ |
| 3.4b | " | 2 × B(C₆H₅)₄⊖ |
| 3.5a | cis/trans H₃C—⊕N(CH₃)₂—(CH₂)₇—NH—C(=O)—[cyclohexane-H]—C(=O)—NH—(CH₂)₁₀—⊕N(CH₃)₂—CH₃ | 2 × BF₄⊖ |
| 3.5b | " | 2 × B(C₆H₅)₄⊖ |
| 4.1a | H₃C—⊕N(CH₃)₂—(CH₂)₇—NH—C(=O)—[cyclohexane-H, =O]—C(=O)—NH—(CH₂)₇—⊕N(CH₃)₂—CH₃ | 2 × BF₄⊖ |

| Compound | Cation | Anion |
|---|---|---|
| 4.1b | " | $2 \times B(C_6H_5)_4^\ominus$ |
| 5.1a | $H_3C-\overset{\oplus}{N}(CH_3)_2-(CH_2)_3-N(CH_3)-C(=O)-C(CH_3)_2-C(=O)-N(H)-(CH_2)_3-\overset{\oplus}{N}(CH_3)_2-CH_3$ | $2 \times BF_4^\ominus$ |
| 5.1b | " | $2 \times B(C_6H_5)_4^\ominus$ |
| 6.1a | $H_3C-\overset{\oplus}{N}(CH_3)_2-(CH_2)_3-N(CH_3)-C(=O)-(CH_2)_2-C(=O)-N(H)-(CH_2)_3-\overset{\oplus}{N}(CH_3)_2-CH_3$ | $2 \times BF_4^\ominus$ |
| 6.1b | " | $2 \times PF_6^\ominus$ |
| 6.1c | " | $2 \times B(C_6H_5)_4^\ominus$ |
| 6.1d | " | $2 \times SCN^\ominus$ |
| 6.1e | " | $2 \times CH_3SO_4^\ominus$ |
| 6.2a | $H-\overset{\oplus}{N}(CH_3)_2-(CH_2)_3-N(CH_3)-C(=O)-(CH_2)_2-C(=O)-N(H)-(CH_2)_3-\overset{\oplus}{N}(CH_3)_2-H$ | $2 \times BF_4^\ominus$ |
| 6.2b | " | $2 \times PF_6^\ominus$ |
| 6.2c | " | $2 \times B(C_6H_5)_4^\ominus$ |
| 6.2d | " | $2 \times SCN^\ominus$ |
| 6.2e | " | $2 \times CH_3SO_4^\ominus$ |

-continued

| Compound | Cation | Anion |
|---|---|---|
| 6.3a | $H_5C_2-{}^{\ominus}N(\!\!+\!\!H_2C)_{\overline{3}}N-C(\!\!+\!\!CH_2)_{\overline{7}}C-N(\!\!+\!\!CH_2)_{\overline{3}}{}^{\ominus}N-C_2H_5$ with CH$_3$/CH$_3$ on left N and CH$_3$/CH$_3$ on right N, H and O on amide | $2 \times BF_4^{\ominus}$ |
| 6.3b | " | $2 \times [B(C_6H_5)_4]^{\ominus}$ |
| 6.4a | $C_2H_5-{}^{\ominus}N(\!\!+\!\!H_2C)_{\overline{3}}N-C(\!\!+\!\!CH_2)_{\overline{7}}C-N(\!\!+\!\!CH_2)_{\overline{3}}{}^{\ominus}N-CH_3$ with C$_2$H$_5$/C$_2$H$_5$ and CH$_3$/C$_2$H$_5$ | $2 \times BF_4^{\ominus}$ |
| 6.4b | " | $2 \times PF_6^{\ominus}$ |
| 6.4c | " | $2 \times SCN^{\ominus}$ |
| 6.4d | " | $2 \times [B(C_6H_5)_4]^{\ominus}$ |
| 6.4e | " | $2 \times CH_3SO_4^{\ominus}$ |
| 6.5a | $H_3C-{}^{\ominus}N(\!\!+\!\!H_2C)_{\overline{3}}N-C(\!\!+\!\!CH_2)_{\overline{7}}C-N(\!\!+\!\!CH_2)_{\overline{3}}{}^{\ominus}N-C_2H_5$ | $2 \times BF_4^{\ominus}$ |
| 6.5b | " | $2 \times [B(C_6H_5)_4]^{\ominus}$ |
| 7.1a | $H_3C-{}^{\ominus}N(\!\!+\!\!H_2C)_{\overline{3}}N-C(\!\!+\!\!CH_2)_{\overline{4}}C-N(\!\!+\!\!CH_2)_{\overline{3}}{}^{\ominus}N-CH_3$ | $2 \times BF_4^{\ominus}$ |

-continued

| Compound | Cation | Anion |
|---|---|---|
| 7.1b | " | 2 × B(C₆H₅)₄⁻ |
| 8.1a | H₃C—⁻N(CH₃)(CH₃)(CH₂)₃N(H)—C(=O)—(CH₂)₈—C(=O)—N(H)—(CH₂)₃N⁺(CH₃)(CH₃)—CH₃ | 2 × BF₄⁻ |
| 8.1b | " | 2 × B(C₆H₅)₄⁻ |
| 9.1a | H₃C—⁻N(CH₃)(CH₃)(CH₂)₃N(H)—C(=O)—C(CH₃)(CH₂CH₃)—CH₂—C(=O)—N(H)—(CH₂)₃N⁺(CH₃)(CH₃)—CH₃ | 2 × BF₄⁻ |
| 9.1b | " | 2 × B(C₆H₅)₄⁻ |
| 10.1a | H₃C—⁻N(CH₃)(CH₃)(CH₂)₃N(H)—C(=O)—O—CH₂—CH₂—O—CH₂—C(=O)—N(H)—(CH₂)₃N⁺(CH₃)(CH₃)—CH₃ | 2 × BF₄⁻ |
| 10.1b | " | 2 × B(C₆H₅)₄⁻ |
| 11.1a | pyromellitic diimide bis[N-(CH₂)₃N⁺(CH₃)₃] | 2 × B(C₆H₅)₄⁻ |

-continued
| Compound | Cation | Anion |
|---|---|---|
| 11.1b | | $2 \times PF_6^{\ominus}$ |
| 11.1c | " | 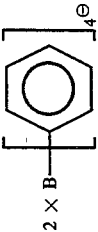 |
| 11.1d | " | $2 \times SCN^{\ominus}$ |
| 11.1e | " | $2 \times CH_3SO_4^{\ominus}$ |
| 11.1f | " | $\frac{2}{3} \times P[Mo_3O_{10}]_4^{3\ominus}$ |
| 12.1a | 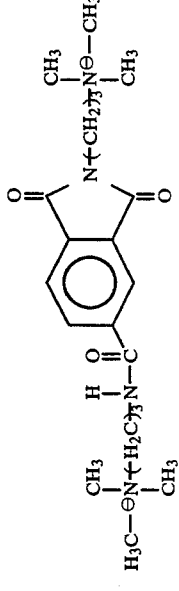 | $2 \times BF_4^{\ominus}$ |
| 12.1b | " | 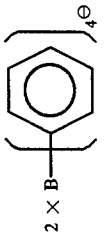 |
| 13.1a | 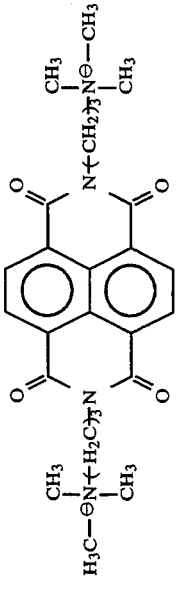 | $2 \times BF_4^{\ominus}$ |
| 13.1b | " | $2 \times PF_6^{\ominus}$ |
| 13.1c | " | 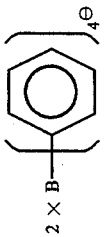 |
| 13.1d | " | $2 \times SCN^{\ominus}$ |

-continued

| Compound | Cation | Anion |
|---|---|---|
| 13.1e | [naphthalenediimide with N(CH₂)₃N⊕(CH₃)₃ groups] | 2 × CH₃SO₄⊖ |
| 13.1f | " | ⅔ × P[Mo₃O₁₀]₄³⊖ |
| 13.2a | [naphthalenediimide with N(CH₂)₃N⊕(CH₃)-imidazole groups] | 2 × BF₄⊖ |
| 13.2b | " | 2 × B(C₆H₅)₄⊖ |
| 13.2c | " | 2 × CH₃SO₄⊖ |
| 13.3a | [naphthalenediimide with N-phenyl-C(O)NH(CH₂)₃N⊕(CH₃)₃ groups] | 2 × BF₄⊖ |
| 13.3b | " | 2 × B(C₆H₅)₄⊖ |
| 13.3.c | " | 2 × CH₃SO₄⊖ |

-continued

| Compound | Cation | Anion |
|---|---|---|
| 14.1a | H₃C—⊖N(H₂C)₃N(CH₃)(CH₃)—C(=O)—H₂C—C(OH)(COOH)—CH₂—C(=O)—N(H)—(CH₂)₃—⊖N(CH₃)(CH₃)—CH₃ | 2 × BF₄⊖ |
| 14.1b | " | 2 × [B(C₆H₅)₄]⊖ |
| 15.1a | Bis-triazinane with two —(CH₂)₃—⊕N(CH₃)₃ groups | 2 × BF₄⊖ |
| 15.1b | " | 2 × [B(C₆H₅)₄]⊖ |
| 16.1a | 1,4-bis(4,4-dimethylpiperazinium-1-ylcarbonyl)benzene | 2 × BF₄⁻ |
| 16.1b | " | 2 · [B(C₆H₅)₄]⁻ |

The preparation of the compounds of the general formula (I) to (III) is carried out in a manner which is known per se and is described in detail in the literature (for example Houben-Weyl, "Methoden der Organischen Chemie (Methods of Organic Chemistry)", Georg Thieme Verlag, 1985, Volume E 5, part 2, pages 924–1134 and loc. cit. 1958, Volume 11/2, pages 591–630).

The compounds (I) are thus prepared, for example, by reaction of the aliphatic, cycloaliphatic, araliphatic or iso- or heterocyclic aromatic dicarboxylic acids or suitable dicarboxylic acid derivatives, such as, for example, esters, amides, acid chlorides or acid anhydrides thereof, with amines or amino compounds which contain at least one tertiary and at least one primary or secondary amino group, in an inert reaction medium or in excess amine as the reaction medium, and subsequent bis-protonation with an inorganic or organic acid or bis-quaternization with a suitable quaternizing reagent. The use of dicarboxylic acid dihalides or of dicarboxylic acid diesters as starting substances is preferred for the preparation of the compounds (I). The aminolysis of dicarboxylic acid diesters, in particular the dimethyl or diethyl ester, with amines at elevated temperature, the alcohol formed being distilled off, is particularly preferred as the preparation process.

The compounds (II) are prepared, for example, by reaction of the aliphatic, cycloaliphatic, araliphatic or iso- or heterocyclic aromatic tetracarboxylic acids or suitable derivatives, such as, for example, esters, amides, acid chlorides or acid anhydrides thereof, in particular monoor dianhydrides thereof, with amines or amino compounds which contain at least one tertiary and at least one primary amino group, and subsequent bis-protonation with an inorganic or organic acid or bis-quaternization with a suitable quaternizing reagent. The reaction can be carried out either under acid catalysis in an aqueous medium or in aliphatic or aromatic carboxylic acids or in mixtures of water and such carboxylic acids. A particularly suitable carboxylic acid is acetic acid. However, the compounds (II) can also be prepared, if appropriate under acid catalysis, in optionally substituted, aliphatic or aromatic hydrocarbons at elevated temperature, the water formed being removed from the circulation. Particularly suitable hydrocarbons which may be mentioned are toluene, xylene, chlorobenzene and o-dichlorobenzene. All diimide-forming tetracarboxylic acids can in principle be used as the tetracarboxylic acids. Aromatic tetracarboxylic acids in which in each case two carboxylic acid groups are in the ortho- or peri-position relative to one another are preferred. The compounds (III) are prepared by a suitable combination of the processes described for the compounds (I) and (II).

All the suitable inorganic and organic acids and all the suitable alkylating agents are in principle possible for the bis-protonation or bis-quaternization. Particularly suitable acids are hydrochloric acid, sulfuric acid and acetic acid. Preferred alkylating agents are alkyl halides and dialkyl sulfates, in particular methyl iodide, methyl chloride and dimethyl and diethyl sulfate. Possible reaction media for carrying out the alkylation are, preferably, inert reaction media, such as, for example, dimethylformamide or aromatic hydrocarbons. However, anhydrous or aqueous alcohols, such as, for example, isobutanol or the isobutanol/water azeotrope having a water content of about 16%, are also suitable. In individual cases, the quaternization can also be carried out in an aqueous medium.

The various salts are prepared by anion exchange, for example by precipitation form an aqueous or aqueous-alcoholic medium, as described in the preparation examples. The particular advantage of the compounds claimed according to the invention is that they are colorless and have a high charge controlling effect, and that this charge controlling effect is constant over a long activation period (up to 24 hours). Thus, for example, a test toner containing only 1 % by weight of the compound (1.1a) shows a charge of $+9$ $\mu$C/g after 10 minutes, $+9$ $\mu$C/g after 30 minutes, $+6$ $\mu$C/g after 2 hours and $+3$ $\mu$C/g after 24 hours (Example 3). The high charge controlling effect becomes all the more clearer if, for example, the charging properties of the pure carrier material Dialec S309 is considered by comparison (comparison example; 10 minutes: $-4$ $\mu$C/g; 30 minutes: $-12$ $\mu$C/g; 2 hours: $-27$ $\mu$C/g; 24 hours: $-48$ $\mu$C/g). As well as establishing the desired charge polarity and level, the compounds claimed according to the invention must also keep the high charge drift of more than 40 $\mu$C/g constant.

Another advantage of the compounds claimed according to the invention is that the charge controlling effect of a compound can be changed in small steps merely by varying the anion. For example, if, instead of the $BF_4^{\ominus}$ salt mentioned in Example 1, the $PF_6^{\ominus}$ salt of the same cation is employed (compound 1.1b), a corresponding test toner shows a charge of $+7$ $\mu$C/g after 10 minutes; $+7$ $\mu$C/g after 30 minutes; $+4$ $\mu$C/g after 2 hours and $+3$ $\mu$C/g after 24 hours (Example 2). It is moreover also possible to reverse the polarity of the symbol of the charge controlling effect by choosing a suitable anion. For example, if the

salt of the cation discussed is employed (compound 1.1c), instead of the positive charge controlling effect, a negative charge controlling effect is found (Example 1; 10 minutes: $-27$ $\mu$C/g; 30 minutes: $-27$ $\mu$C/g; 2 hours: $-25$ $\mu$C/g; 24 hours: $-23$ $\mu$C/g). The charge controlling effect of the compounds claimed according to the invention is moreover highly insensitive to variations in atmospheric humidity (Example 3).

It is of great importance in practice that the compounds claimed according to the invention are chemically inert and readily compatible with carrier materials, such as, for example, styrene acrylates, polyesters, epoxides, polyurethanes and the like. In addition, the compounds are stable to heat and can therefore be incorporated into the customary carrier materials without difficulty using the customary processes (extrusion, kneading) under the customary conditions (temperatures of between 100° C. and 200° C.). the synthesis of the compounds claimed according to the invention is not particularly involved and the products are obtained in a high purity.

The compounds used according to the invention are as a rule incorporated homogeneously in a concentration of about 0.01 to about 30 percent by weight, preferably about 0.1 to about 5.0 percent by weight, into the particular carrier material in a known manner, for example by kneading in or extrusion. The charge controller for toners or charge-improving agent for powders and paints for surface coating, in particular for triboelectrically or electrokinetically sprayed powder paints, can be added here as dried and ground powders, dispersions or solutions, press-cakes, a masterbatch, as compounds absorbed onto suitable carriers, such as, for example, silica gel, $TiO_2$ or $Al_2O_3$, form aqueous or nonaqueous solution, or in another form. The compounds employed according to the invention can likewise in principle also already been added during the preparation of the particular binders, that is to say in the course of the polymerization, polyaddition or polycondensation thereof. The level of the electrostatic charge of the electrophotographic toners in which the charge controllers claimed according to the invention were incorporated homogeneously was measured by standard test systems under identical conditions (such as the same dispersion times, same particle size distribution, same particle shape) at room temperature and 50% relative atmospheric humidity. The particular toner was conditioned in a climatic chamber for the measurement at room temperature and 90% relative atmospheric humidity. The toner was activated in a two-component developer by swirling with a carrier (3 parts by weight of toner per 97 parts by weight of carrier) on a roller bench (150 revolutions per minute). The electrostatic charge was then measured on a customary q/m measuring stand (cf. J.H. Dessauer, H.E. Clark, "Xerography and related Processes", Focal Press, N.Y., 1965, page 289). The particle size has a great influence on the determination of the q/m value, which is why strict attention was paid to a uniform particle size distribution of the toner samples obtained by sizing.

The following examples serve to illustrate the invention without limiting it thereto. The parts stated are parts by weight.

PREPARATION EXAMPLES

EXAMPLE A

Amide Formation 149.2 g (0.73 mol) of terephthaloyl dichloride are stirred into 3.5 l of anhydrous toluene, and 180.0 g (1.76 mol) of 3-dimethylamino-1-propylamine are then added dropwise at 20° to 30° C. in the course of 30 minutes. The mixture is stirred at this temperature for 5 hours, subsequently heated at 50° to 60° C. and 70° to 80° C. for in each case 1 to 2 hours and then heated under reflux for 4 hours. The resulting product is filtered off with suction at 20° to 30° C., washed with toluene and dried at 100° C. in a vacuum drying cabinet. 292.4 g (0.72 mol) of the bisamide are obtained in the form of the bishydrochloride. The product is dissolved in 450 ml of water, and 180 g of 33 % strength sodium hydroxide solution are added at 0° to 5° C. in the course of 30 minutes. During this operation, the bisamide precipitates out in coarsely crystalline form. After the mixture has been stirred at 0° to 5° C. for one hour, the product is filtered off with suction, washed with 90 ml of ice-water and dried at 100° C. in a vacuum cabinet.

Characterization:

White powder, melting point 172°–174° C.

$^1$H-NMR (in DMSO-$d_6$): 1.65 (quintet, 4 methylene-H), 2.13 (singlet, 12 methyl-H), 2.28 (triplet, 4 methylene-H), 3.30 (quartet, 4 methylene-H), 7.90 (singlet, 4 phenylene-H), 8.63 (triplet, 2 amide-H) ppm.

Quaternization 66.8 g (0.2 mol) of the amide are stirred into 1.6 l of toluene, and 100.8 g (0.8 mol) of dimethyl sulfate are added at 20° to 30° C. in the course of 10 minutes. The mixture is stirred at 20° to 30° C. for 1 hour and then heated under reflux for 5 hours. After cooling to 20° to 30° C., the product is filtered off with suction, washed with toluene and dried at 100° C. in a vacuum cabinet.

Characterization:

White powder, melting point 180° C.

$^1$H-NMR (in $D_2O$): 2.18 (multiplet, 4 methylene-H), 3.20 (singlet, 18 methyl-H), 3.50 (multiplet, 8 methylene-H), 3.75 (singlet, 6 methyl-H), 7.88 (singlet, 4 phenylene-H) ppm.

Anion Exchange

A solution of 13.7 g (40 mmol) of sodium tetraphenylborate in 50 ml of water is added dropwise to 100 ml of a solution of 10.0 g (17 mmol) of the quaternized compound at room temperature, while stirring. During this operation, compound 1.1c precipitates out as a white precipitate. The precipitate is filtered off with suction, washed with water and dried in a circulating air cabinet at 60° C.

Characterization:

White powder, melting point 255° C.

$^1$H-NMR (in DMSO-$d_6$): 1.98 (multiplet, 4 methylene-H), 3.03 (singlet, 18 methyl-H), 3.38 (multiplet, 8 methylene-H), 6.96 (multiplet, 40 phenyl-H), 7.95 (singlet, 4 phenylene-H), 8.64 (triplet, 2 amide-H) ppm.

EXAMPLE B

Amide Formation

The amide was formed as described in Example A.

Salt Formation 5.0 g (15 mmol) of the amide are suspended in 50 ml of water, and 2N acetic acid is added until a pH of 7 is reached, during which the amine dissolves. A solution of 13.7 g (40 mmol) of sodium tetraphenylborate in 50 ml of water is then added dropwise, whereupon the product precipitates out as a thick white precipitate. The reaction mixture is stirred at room temperature for 30 minutes, the precipitate is filtered off with suction and washed with water and finally the reaction product, compound 1.2c is dried at 60° C. in a circulating air cabinet.

Characterization:

White powder, melting point 197° C.

$^1$H-NMR (in DMSO-$d_6$): 1.85 (multiplet, 4 methylene-H), 2.71 (singlet, 12 methyl-H), 3.00 (multiplet, 4 methylene-H), 3.35 (multiplet, 4 methylene-H), 6.96 (multiplet, 40 phenyl-H), 7.93 (singlet, 4 phenylene-H), 8.63 (triplet, 2 amide-H ) ppm.

EXAMPLE C

Amide Formation 109.5 g (0.75 mol) of dimethyl succinate are dissolved in 459 g (4.5 mol) of 3-dimethylamino-1-propylamine. The mixture is then heated under reflux for 10 hours. Since the boiling point drops considerably due to the rapid onset of splitting off of methanol, it is ensured, by occasional distillation of a methanol-amine mixture, that the temperature in the gas phase remains above 125° C. Toward the end of the reaction time, the temperature in the gas phase is above 130° C. About 200 g of methanol- /amine mixture are distilled off in the course of the reaction. The mixture is then cooled to 20° to 30° C. and the reaction product which has crystallized out is filtered off with suction. Further product can be precipitated out of the filtrate by three-fold dilution with benzine. The product is washed free from amine with benzine and dried at 100° C. in a vacuum cabinet.

Characterization:

White powder, melting point 126°–128° C. $^1$H-NMR (in DMSO-$d_6$): 1.48 (quintet, 4 methylene-H), 2.08 (singlet, 12 methyl-H), 2.20 (triplet, 4 methylene-H), 2.25 (singlet, 4 methylene-H), 3.05 (quartet, 4 methylene-H), 7.78 (triplet, 2 amide-H) ppm.

Quaternization 85.8 g (0.3 mol) of the amide are introduced into 610 ml of anhydrous dimethylformamide. A clear solution rapidly forms at room temperature. 189 g (1.5 mol) of dimethyl sulfate are then added dropwise at 30° to 40° C. in the course of about 15 minutes. After a short time, a thick crystal slurry is formed, which changes into a readily stirtable suspension on heating to 60° C. The suspension is subsequently stirred at 60° to 70° C. for 5 hours and, after cooling to 0° to 5° C., the product is filtered off with suction. It is washed thoroughly with toluene and dried in a vacuum cabinet at 100° C.

Characterization:

White powder, melting point 152° C. $^1$H-NMR (in DMSO-$d_6$): 1.85 (multiplet, 4 methylene-H), 2.33 (singlet, 4 methyl-H), 3.05 (singlet, 18 methyl-H), 3.20 (multiplet, 8 methylene-H), 3.40 (singlet, 6 methyl-H), 7.95 (triplet, 2 amide-H) ppm.

Anion Exchange 10.0 g (18.5 mmol) of the quaternized product were precipitated with 13.7 g (40 mmol) of sodium tetraphenylborate analogously to the salt formation described in Example A, to give the compound 6.1c.

Characterization:

White powder, melting point 245° C.

$^1$H-NMR (in DMSO-$d_6$): 1.81 (multiplet, 4 methylene-H), 2.37 (singlet, 4 methylene-H), 3.02 (singlet, 18 methyl-H), 3.12 (quartet, 4 methylene-H), 3.24 (multiplet, 4 methylene-H), 6.97 (multiplet, 40 phenyl-H), 7.90 (triplet, 2 amide-H) ppm.

EXAMPLE D

Amide Formation

The amide was formed as described in Example C.

Salt Formation

The salt formation with 13.7 g (40 mmol) of sodium tetraphenylborate was carried out analogously to the salt formation described in Example B, 5.0 g (17.5 mmol) of the amide described in Example C being employed. Compound 6.2c is obtained as the product.

Characterization:

White powder, melting point 183° C. 1H—NMR (in DMSO-$d_6$): 1.72 (multiplet, 4 methylene-H), 2.38 (singlet, 4 methylene-H), 2.68 (singlet, 12 methyl-H), 2.95 (multiplet, 4 methylene-H), 3.12 (quartet, 4 methylene-H), 7.01 (multiplet, 40 phenyl-H), 7.92 (triplet, 2amide-H) ppm.

EXAMPLE E

Imide Formation 218.0 g (1.0 mol) of pyromellitic dianhydride are stirred in 1.2 l of glacial acetic acid, and 306 g (3.0 mol) of 3-dimethylamino-1-propylamine are added dropwise at 40° to 50° C., while cooling. The mixture is then heated under reflux for 3 hours, 920 ml of o-dichlorobenzene are added and the majority of the glacial acetic acid is distilled off. The mixture is then heated, while passing over a stream of nitrogen and distilling of the residual glacial acetic acid, until the boiling point of o-dichlorobenzene is reached, and heating is continued under reflux for 6 hours. After the mixture has been cooled to 20° to 30° C., the product which has precipitated out is filtered off with suction, washed with benzine and dried at 100° C. in a vacuum cabinet.

Characterization:

White powder, melting point 186°–188° C.

$^1$HN13 MR (in DMSO-$d_6$): 1.75 (quintet, 4 methylene-H), 2.08 (singlet, 12 methyl-H), 2.25 (triplet, 4 methylene-H), 3.68 (triplet, 4 methylene-H), 8.15 (singlet, 2 phenylene-H) ppm.

Quaternization 77.2 g (0.2 mol) of the imide are stirred in 600 ml of dimethylformamide, and 126.0 g (1.0 mol) of dimethyl sulfate are added dropwise at 30° to 40° C. in the course of 20 minutes, while cooling. The mixture is heated at 130° to 135° C. for 5 hours and, after cooling to 20° to 30° C., the product is filtered off with suction. The product is washed with toluene and dried at 100° C. in a vacuum cabinet.

Characterization:

White powder, melting point 197° C.

$^1$H—NMR (in $D_2O$): 2.23 (multiplet, 4 methylene-H), 3.15 (singlet, 18 methyl-H), 3.48 (multiplet, 4 methylene-H), 3.73 (singlet, 6 methyl-H), 3.88 (triplet, 4 methylene-H), 8.33 (singlet, 2 phenylene-H) ppm.

Anion Exchange

The anion exchange with 13.7 g (40 mmol) of sodium tetraphenylborate is carried out analogously to the anion exchange described in Example A, 10.0 g (16 mmol) of the quaternized compound mentioned above being employed, to give the compound 11.1c as the product.

Characterization:

White powder, melting point 295° C.

$^1$H—NMR (in DMSO-$d_6$): 2.08 (multiplet, 4 methylene-H), 2.97 (singlet, 18 methyl-H), 3.36 (multiplet, 4 methylene-H), 3.70 (triplet, 4 methylene-H), 6.98 (multiplet, 40 phenyl-H), 8.28 (singlet, 2 phenylene-H) ppm.

EXAMPLE F

Imide Formation 71.5 g (0.25 mol) of naphthalene-1,4,5,8-tetracarboxylic acid 1,8-monoanhydride are stirred into 500 ml of glacial acetic acid, and 93.8 g (0.75 mol) of N-(3-aminopropyl)-imidazole are added dropwise at 40° to 50° C., while cooling gently. The mixture is then heated under reflux for 6 hours. The resulting solution of the reaction product is poured into 2.5 l of water, and 1.01 kg of 33% strength sodium hydroxide solution are then added dropwise at 20° to 30° C., while cooling, so that the product precipitates out. The product is filtered off with suction, washed thoroughly with water and dried at 100° C. in a vacuum cabinet.

Characterization:

White powder, melting point 260°–263° C.

Quaternization 96.4 g (0.2 mol) of the imide are stirred into 600 ml of dimethylformamide, and 189.0 g (1.5 mol) of dimethyl sulfate are added dropwise at 30° to 40° C. in the course of 10 minutes, while cooling gently. The mixture is then stirred at 130° to 135° C. for 5 hours. After the mixture has been cooled to 20° to 30° C., the product, compound 13.2c is filtered off with suction, washed with 100 ml of dimethylformamide and then with toluene and dried at 100° C. in a vacuum cabinet.

Characterization:

White powder, melting point 261° C.

$^1$H—NMR (in $D_2O$): 2.35 (quintet, 4 methylene-H), 3.68 (singlet, 6 methyl-H), 3.95 (singlet, 6 methyl-H), 4.10 (triplet, 4 methylene-H), 4.39 (triplet, 4 methylene-H), 7.60 (multiplet, 4 imidazoyl-H), 8.40 (singlet, 4 naphthylene-H), 8.86 (singlet, 2 imidazoyl-H)ppm.

USE EXAMPLES

EXAMPLE 1

One part of the terephthalic acid derivative 1.1c (for the synthesis of the compound, see Preparation Example A) was dispersed homogeneously in 99 parts of toner binder ($^R$Dialec S 309 from Diamond Shamrock (styrene/methacrylic copolymer)) by means of a kneader from Werner & Pfleiderer (Stuttgart) for 30 minutes. The dispersion was then ground on a 100 LU universal laboratory mill (Alpine, Augsburg) and subsequently classified on a 100 MZR centrifugal sizer (Alpine).

The desired particle fraction was activated with a carrier of magnetite particles of size 50 to 200 μm coated with styrene/methacrylic copolymer 90:10, of the type "90 μm Xerographic Carrier" from Plasma Materials Inc.

The measurement is carried out on a customary q/m measuring stand (in this context cf. J. H. Dessauer, H. E. Clark "Xerography and related Processes", Focal Press, N.Y. 1965 page 289); using a sieve of mesh width 25 μm (508 mesh per inch), Gebrüder Kufferath, Düren, it was ensured that no carrier can be entrained when the toner is blown out. The measurements were made at room temperature and 50% relative atmospheric humidity, deviating experimental conditions being noted in the examples in question.

The following q/m values [μC/g] were measured as a function of the activation time:

| Activation time | [μC/g] |
| --- | --- |
| 10 minutes | −27 |
| 30 minutes | −27 |
| 2 hours | −25 |
| 24 hours | −23 |

EXAMPLE 2

1 part of the terephthalic acid derivative 1.1b (for the synthesis, see below) was incorporated homogeneously into 99 parts of toner binder as described in Example 1. The following q/m values [μC/g] were measured as a function of the activation time:

| Activation time | [μC/g] |
| --- | --- |
| 10 minutes | +7 |
| 30 minutes | +7 |
| 2 hours | +4 |
| 24 hours | +3 |

Synthesis

The preparation of the amide and the quaternization were carried out analogously to Preparation Example A. Instead of NaB-(phenyl)$_4$, the KPF$_6$ salt was employed for the anion exchange.

Characterization:

White powder, melting point 265° C.

$^1$H—NMR (in DMSO-d$_6$): 1.98 (multiplet, 4 methylene-H), 3.04 (singlet, 18 methyl-H), 3.37 (multiplet, 8 methylene-H), 7.92 (singlet, 4 phenylene-H), 8.63 (triplet, 2 amide-H) ppm.

EXAMPLE 3

1 part of the terephthalic acid derivative 1.1a (for the synthesis, see below) were incorporated homogeneously into 99 parts of toner binder as described in Example 1. The following q/m values [μC/g] were measured as a function of the activation time:

| Activation time | [μC/g] |
| --- | --- |
| 10 minutes | +9 |
| 30 minutes | +9 |
| 2 hours | +6 |
| 24 hours | +3 |

The following q/m values [μ/C/g] were determined at 90% relative atmospheric humidity:

| Activation time | [μC/g] |
| --- | --- |
| 10 minutes | +6 |
| 30 minutes | +7 |
| 2 hours | +7 |
| 24 hours | +3 |

Synthesis

The preparation of the amide and the subsequent quaternization were carried out analogously to Preparation Example A, the solution being concentrated to 30 ml and cooled to 2° C. to obtain the precipitate.

Instead of NaB-(phenyl)$_4$, an NaBF$_4$ salt was employed for the anion exchange.

Characterization:

White powder, melting point 228° C.

$^1$H—NMR (in DMSO-d$_6$): 1.99 (multiplet, 4 methylene-H), 3.05 (singlet, 18 methyl-H), 3.38 (multiplet, 8 methylene-H), 7.93 (singlet, 4 phenylene-H), 8.62 (triplet, 2 amide-H) ppm.

EXAMPLE 4

1 part of the terephthalic acid derivative 1.2c (for the synthesis, see Preparation Example B) was incorporated homogeneously into 99 parts of toner binder as described in Example 1. The following q/m values [μC/g] were measured as a function of the activation time:

| Activation time | [μC/g] |
| --- | --- |
| 10 minutes | −27 |
| 30 minutes | −32 |

| Activation time | [μC/g] |
| --- | --- |
| 2 hours | −32 |
| 24 hours | −31 |

EXAMPLE 5

One part of the succinic acid derivative 6.1c (for the synthesis, see Preparation Example C) was incorporated homogeneously into 99 parts of toner binder as described in Example 1. The following q/m values [μC/g] were measured as a function of the activation time:

| Activation time | [μC/g] |
| --- | --- |
| 10 minutes | −31 |
| 30 minutes | −34 |
| 2 hours | −33 |
| 24 hours | −22 |

EXAMPLE 6

One part of the succinic acid derivative 6.1b (for the synthesis, see below) were incorporated homogeneously into 99 parts of toner binder as described in Example 1. The following q/m values ]μC/g] were measured as a function of the activation time:

| Activation time | [μC/g] |
| --- | --- |
| 10 minutes | −5 |
| 30 minutes | −7 |
| 2 hours | −8 |
| 24 hours | −7 |

Synthesis

The preparation of the amide and the quaternization were carried out analogously to Preparation Example C.

Instead of NaB-(phenyl)$_4$, a KPF$_6$ salt was employed for the anion exchange.

Characterization:

White powder, melting point 208° C.

$^1$H—NMR (in DMSO-d$_6$): 1.83 (multiplet, 4 methylene-H), 2.35 (singlet, 4 methylene-H), 3.02 (singlet, 18 methyl-H), 3,12 (quartet, 4 methylene-H), 8.25 (multiplet, 4 methylene-H), 7.86 (triplet, 2 amide-H) ppm.

EXAMPLE 7

One part of the succinic acid derivative 6.2c (for the amide formation, see Preparation Example C, salt formation analogous to Preparation Example B) was incorporated homogeneously into 99 parts of toner binder as described in Example 1. The following q/m values [μC/g] were measured as a function of the activation time:

| Activation time | [μC/g] |
| --- | --- |
| 10 minutes | −35 |
| 30 minutes | −38 |
| 2 hours | −40 |
| 24 hours | −32 |

EXAMPLE 8

One part of the 1,4-cyclohexanedicarboxylic derivative 3.2b (for the synthesis, see below) was incorporated homogeneously into 99 parts of toner binder as described in Example 1. The following q/m values [μC/g] were measured as a function of the activation time:

| Activation time | [μC/g] |
| --- | --- |
| 10 minutes | −6 |
| 30 minutes | −8 |
| 2 hours | −11 |
| 24 hours | −12 |

Synthesis

The preparation of the amide and the quaternization were carried out analogously to Preparation Example C, dimethyl 1,4-cyclohexanedicarboxylate being employed instead of dimethyl succinate.

The KPF$_6$ salt was employed for the anion exchange.

Characterization:

White powder, melting point 298° C.

$^1$H-NMR (in DMSO-d$_6$): 1.35 (multiplet, 4 methylene-H), 1.8 (multiplet, 8 cyclohexylene-H), 2.05 (multiplet, 2 cyclohexylene-H), 3.05 (singlet, 18 methyl-H), 3.25 (multiplet, 4 methylene-H), 3.25 (multiplet, 4 methylene-H), 7.78 (triplet, 2 amide-H) ppm.

EXAMPLE 9

One part of the 1,4-cyclohexanedicarboxylic acid derivative 3.2c (for the synthesis, see below) was incorporated homogeneously into 99 parts of toner binder as described in Example 1. The following q/m values [μC/g] were measured as a function of the activation time:

| Activation time | [μC/g] |
| --- | --- |
| 10 minutes | −35 |
| 30 minutes | −37 |
| 2 hours | −37 |
| 24 hours | −40 |

Synthesis

The preparation of the amide and the quaternization were carried out analogously to Preparation Example C, dimethyl 1,4-cyclohexanedicarboxylate being employed instead of dimethyl succinate.

Instead of KPF$_6$, the NaB-(phenyl)$_4$ salt was employed for the anion exchange.

Characterization:

White powder, melting point 255° C.

$^1$H—NMR (in DMSO-d$_6$): 1.35 (multiplet, 4 methylene-H), 1.8 (multiplet, 8 cyclohexylene-H), 2.05 (multiplet, 2 cyclohexylene-H), 3.03 (singlet, 18 methyl-H), 3.1 (multiplet, 4 methylene-H), 3.25 (multiplet, 4 methylene-H), 6.95 (multiplet, 40 phenyl-H), 7.8 (triplet, 2 amide-H) ppm.

EXAMPLE 10

1 part of the pyromellitic acid derivative 11.1c (for the synthesis, see Preparation Example E) was incorporated homogeneously into 99 parts of toner binder as described in Example 1.

The following q/m values [μC/g] were measured as a function of the activation time:

| Activation time | [μC/g] |
| --- | --- |
| 10 minutes | −13 |
| 30 minutes | −20 |
| 2 hours | −22 |
| 24 hours | −18 |

EXAMPLE 11

1 part of the pyromellitic acid derivative 11.1a (for the synthesis, see below) was incorporated homogeneously into 99 parts of toner binder as described in Example 1. The following q/m values [μC/g] were measured as a function of the activation time:

| Activation time | [μC/g] |
| --- | --- |
| 10 minutes | −3 |
| 30 minutes | −5 |
| 2 hours | −8 |
| 24 hours | −9 |

Synthesis

The preparation of the imide and the quaternization were carried out analogously to Preparation Example E. Instead of NaB-(phenyl)4, an NaBF$_4$ salt was employed for the anion exchange.

Characterization:

White powder, melting point >300° C.

$^1$H—NMR (in DMSO-d$_6$): 2.12 (multiplet, 4 methylene-H), 3.05 (singlet, 18 methyl-H), 3.35 (multiplet, 4 methylene-H), 3.71 (triplet, 4 methylene-H), 8.26 (singlet, 2 phenylene-H) ppm.

EXAMPLE 12

1 part of the pyromellitic acid derivative 11.1d (for the synthesis, see below) was incorporated homogeneously into 99 parts of toner binder as described in Example 1. The following q/m values [μC/g] were measured as a function of the activation time:

| Activation time | [μC/g] |
| --- | --- |
| 10 minutes | +9 |
| 30 minutes | +8 |
| 2 hours | +4 |
| 24 hours | +0.3 |

Synthesis

The preparation of the imide and the quaternization were carried out analogously to Preparation Example E. Instead of NaB-(phenyl)4, a KSCN salt was employed for the anion exchange.

Characterization:

White powder, melting point 285° C.

$^1$H—NMR (in DMSO-d$_6$): 2.10 (multiplet, 4 methylene-H), 3.06 (singlet, 18 methyl-H), 3.41 (multiplet, 4 methylene-H), 3.70 (triplet, 4 methylene-H), 8.24 (singlet, 2 phenylene-H) ppm.

EXAMPLE 13

1 part of the pyromellitic acid derivative 11.1b (for the synthesis, see below) was incorporated homogeneously into 99 parts of toner binder as described in Example 1. The following q/m values [μC/g] were measured as a function of the activation time:

| Activation time | [μC/g] |
| --- | --- |
| 10 minutes | −3 |
| 30 minutes | −8 |
| 2 hours | −11 |
| 24 hours | −11 |

Synthesis

The preparation of the imide and the quaternization were carried out analogously to Preparation Example E. Instead of NaB-(phenyl)4, the KPF$_6$ salt was employed for the anion exchange.

Characterization:

White powder, melting point >300° C.

$^1$H—NMR (in DMSO-d$_6$): 2.08 (multiplet, 4 methylene-H), 3.03 (singlet, 18 methyl-H), 3.38 (multiplet, 4 methylene-H), 3.72 (triplet, 4 methylene-H), 8.27 (singlet, 2 phenylene-H) ppm.

EXAMPLE 14

1 part of the pyromellitic acid derivative 11.1a (for the synthesis, see below) was incorporated homogeneously into 99 parts of toner binder as described in Example 1. The following q/m values [μC/g] were measured as a function of the activation time:

| Activation time | [μC/g] |
| --- | --- |
| 10 minutes | −7 |
| 30 minutes | −16 |
| 2 hours | −25 |
| 24 hours | −32 |

Synthesis

The preparation of the imide and the quaternization were carried out analogously to Preparation Example E. Instead of NaB-(phenyl)4, an Na$_3$[P(Mo$_3$O$_{10}$)$_4$] salt was employed for the anion exchange.

Characterization:

Yellowish powder, melting point >300° C.

$^1$H—NMR (in DMSO-d$_6$): 2.13 (multiplet, 4 methylene-H), 3.10 (singlet, 18 methyl-H), 3.42 (multiplet, 4 methylene-H), 3.73 (triplet, 4 methylene-H), 8.22 (singlet, 2 phenylene-H) ppm.

EXAMPLE 15

1 part of the pyromellitic acid derivative 11.1e (the synthesis of the methyl sulfate salt is described in Preparation Example E) was incorporated into 99 parts of toner binder as described in Example 1. The following q/m values [μC/g] were measured as a function of the activation time:

| Activation time | [μC/g] |
| --- | --- |
| 10 minutes | +7 |
| 30 minutes | +7 |
| 2 hours | +6 |
| 24 hours | +3 |

EXAMPLE 16

1 part of the naphthalenetetracarboxylic acid derivative 13.2c (for the synthesis, see Preparation Example F) was incorporated homogeneously into 99 parts of toner binder as described in Example 1. The following q/m values [μC/g] were measured as a function of the activation time:

| Activation time | [μC/g] |
| --- | --- |
| 10 minutes | +12 |
| 30 minutes | +10 |
| 2 hours | +7 |
| 24 hours | +4 |

EXAMPLE 17

1 part of the naphthalenetetracarboxylic acid derivative 13.3c (for the synthesis, see below) was incorporated homogeneously into 99 parts of toner binder as described in Example 1. The following q/m values [μC/g] were measured as a function of the activation time:

| Activation time | [μC/g] |
| --- | --- |
| 10 minutes | −1 |
| 30 minutes | −1 |
| 2 hours | −7 |
| 24 hours | −10 |

Synthesis

The preparation of the imide and the quaternization were carried out analogously to Preparation Example F, 2 parts of

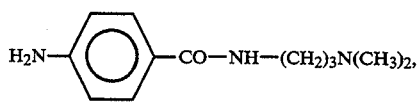

prepared by reaction of 4-nitrobenzoyl chloride with 3-dimethylamino-1-propylamine and subsequent reduction of the nitro group, being employed as the amine component.

Characterization:

White powder, melting point >300° C. (decomposition)

$^1$H—NMR (in DMSO-d$_6$): 2.6 (multiplet, 4 methylene-H), 3.5 (singlet, 18 methyl-H), 3.8 (multiplet, 8 methylene-H), 4.1 (singlet, 6 methyl-H), 7.6 (multiplet, 4 phenyl-H), 8.2 (multiplet, 4 phenyl-H), 8.9 (singlet, 4 naphthyl-H) ppm.

EXAMPLE 18

1 part of the naphthalenetetracarboxylic acid derivative 13.1a (for the synthesis, see below) was incorporated homogeneously in 99 parts of toner binder as described in Example 1. The following q/m values [μC/g] were measured as a function of the activation time:

| Activation time | [μC/g] |
| --- | --- |
| 10 minutes | +7 |
| 30 minutes | +4 |
| 2 hours | +1 |
| 24 hours | −2 |

Synthesis

The preparation of the imide and the quaternization were carried out as described in Preparation Example F, 2 parts of 3-dimethylamino-1-propylamine being employed as the amine component. The anion exchange was carried out with NaBF$_4$ analogously to that described in Example A.

Characterization:

White powder, melting point >300° C. $^1$H—NMR (in DMSO-d$_6$): 2.20 (multiplet, 4 methylene-H), 3.05 (singlet, 18 methyl-H), 3.46 (multiplet, 4 methylene-H), 4.19 (triplet, 4 methylene-H), 8.68 (singlet, 2 naphthylene-H) ppm.

EXAMPLE 19

1 part of the naphthalenetetracarboxylic acid derivative 13.1c (for the synthesis, see below) was incorporated homogeneously into 99 parts of toner binder as described in Example 1. The following q/m values [μC/g] were measured as a function of the activation time:

| Activation time | [μC/g] |
| --- | --- |
| 10 minutes | −3 |
| 30 minutes | −7 |
| 2 hours | −11 |
| 24 hours | −14 |

Synthesis

The preparation of the imide and the quaternization were carried out as described in Preparation Example F, 2 parts of 3-dimethylamino-1-propylamine being employed as the amine component.

The anion exchange was carried out with NaB-(phenyl) as described in Example A.

Characterization:

White powder, melting point >287° C. (decomposition) $^1$H—NMR (in DMSO-d$_6$): 2.13 (multiplet, 4 methylene-H), 3.00 (singlet, 18 methyl-H), 3.45 (multiplet, 4 methylene-H), 4.16 (triplet, 4 methylene-H), 6.90 (multiplet, 40 phenyl-H), 8.71 (singlet, 2 naphthylene-H) ppm.

COMPARISON EXAMPLE TO EXAMPLES 1 TO 19

100 parts of the toner binder Dialec S 309 described in Example 1 were kneaded in a kneader without further additives for 30 minutes as described in Example 1, and were then ground, classified and measured on a q/m measuring stand.

The following q/m values [μC/g] were determined as a function of the activation time:

| Activation time | [μC/g] |
| --- | --- |
| 10 minutes | −4 |
| 30 minutes | −12 |
| 2 hours | −27 |
| 24 hours | −48 |

EXAMPLE 20

1 part of the terephthalic acid derivative 1.1a employed in Example 3 was incorporated homogeneously into 99 parts of a powder paint binder (®Alftalat AN 757 from Hoechst AG, polyester resin) by a procedure analogous to that described in Example 1. The following q/m values [μC/g] were measured as a function of the activation time:

| Activation time | [μC/g] |
|---|---|
| 10 minutes | −7 |
| 30 minutes | −8 |
| 2 hours | −8 |
| 24 hours | −6 |

COMPARISON EXAMPLE TO EXAMPLE 20

100 parts of the powder paint binder Alftalat AN 757 described in Example 20 were kneaded in a kneader without further additives for 30 minutes as described in Example 1, and then ground, classified and measured on a q/m measuring stand. The following q/m values [μC/g] were measured as a function of the activation time

| Activation time | [μC/g] |
|---|---|
| 10 minutes | −35 |
| 30 minutes | −32 |
| 2 hours | −24 |
| 24 hours | −13 |

EXAMPLE 21

1 part of the compound 16.1a (for the synthesis, see below) was incorporated homogeneously into 99 parts of Dialec S 309 as described in Example 1. The following q/m values [μC/g] were measured as a function of the activation time:

| Activation time | [μC/g] |
|---|---|
| 10 minutes | +21 |
| 30 minutes | +19 |
| 2 hours | +16 |
| 24 hours | +9 |

Synthesis 101.5 g (0.5 mol) of terephthaloyl dichloride are dissolved in 2.3 l of toluene, and 120 g (1.2 mol) of N-methylpiperazine are added dropwise at 20° to 30° C., while cooling. The mixture is stirred at 20° to 30° C. for 1 hour, subsequently heated up to the reflux temperature over hours and boiled under reflux for 4 hours. After the mixture has been cooled to room temperature, the product is filtered off with suction, washed with toluene and dried. The dry product is dissolved in 400 ml of water, the solution is clarified with active charcoal and kieselguhr and the bisamide is precipitated by addition of 33% strength NaOH at 0° to 5° C. The bisamide is filtered off with suction, washed with water and dried at 100° C. in vacuo. 66 g (0.2 mol) of the dry bisamide are dissolved in 640 ml of dimethylformamide, and 76 ml (0.8 mol) of dimethyl sulfate are added dropwise at room temperature over a period of 15 minutes, while cooling gently.

The mixture is then heated at 60° to 70° C. for 5 hours and the product is subsequently filtered off with suction at 0° to 5° C., washed with toluene and dried at 100° C. in vacuo.

Yield 109 g (quantitative yield) of white powder

Molecular weight 582
Melting point >300° C.
$^1$H—NMR (in $D_2O$): 3.28 (singlet, 12 methyl-H), 3.53 (multiplet, 8 H piperazino-H), 3.73 (singlet, methyl-H of the methyl sulfate anion, mostly hydrolyzed to hydrogen sulfate), 3.88 (multiplet, 4 piperazino-H), 4.13 (multiplet, 4 piperazino-H), 7.60 (singlet, 4 phenylene-H) ppm. 5.0 g (9 mmol) of the above compound are dissolved in 20 ml of water at room temperature. 2.2 g (20 mmol) of sodium tetrafluoroborate in 25 ml of water are then slowly added, during which the reaction mixture becomes very thick due to the crystals which precipitate out. The mixture is diluted to 250 ml with water and the colorless crystals are then filtered off with suction. After washing with water, the product is dried at 100° C. in a vacuum drying cabinet.

Yield: 3.8 g (79.1 % of theory) of the compound 16.1a, colorless crystals
Molecular weight: 534
Melting point: >300° C. $^1$H—NMR (in DMSO-$d_6$) 3.20 (singlet, 12 methyl-M), 3.48 (singlet, 8 piperazino-H), 3.83 (singlet, 8 piperazino-H), 7.56 (singlet, 4 phenylene-H) ppm.

EXAMPLE 22

1 part of the compound 16.1a described in Example 21 was incorporated homogeneously into 99 parts of Alftalat AN 757 powder paint binder by a procedure analogous to that described in Example 1. The following q/m values [μC/g] were measured as a function of the activation time:

| Activation time | [μC/g] |
|---|---|
| 10 minutes | −26 |
| 30 minutes | −22 |
| 2 hours | −16 |
| 24 hours | −9 |

EXAMPLE 23

1 part of the compound 16.1a described in Example 21 was incorporated homogeneously into 99 parts of Crylcoat 430 powder paint binder (polyester resin containing carboxyl groups from UCB, Belgium) by a procedure analogous to that described in Example 1. The following q/m values [μC/g] were measured as a function of the activation time:

| Activation time | [μC/g] |
|---|---|
| 10 minutes | −7 |
| 30 minutes | −8 |
| 2 hours | −9 |
| 24 hours | −7 |

COMPARISON EXAMPLE TO EXAMPLE 23

100 parts of the Crylcoat 430 powder paint binder described in Example 23 were kneaded in a kneader without further additives for 30 minutes, as described in Example 1, and were then ground, classified and measured on a q/m stand. The following q/m values [μC/g] were measured as a function of the activation time:

| Activation time | [μC/g] |
|---|---|
| 10 minutes | −20 |
| 30 minutes | −15 |

-continued

| Activation time | [μC/g] |
|---|---|
| 2 hours | −9 |
| 24 hours | −7 |

EXAMPLE 24

One part of the compound 16.1b (for the synthesis, see below) was incorporated homogeneously into 99 parts of Dialec S 309 as described in Example 1. The following q/m values [μC/g] were measured as a function of the activation time:

| Activation time | [μC/g] |
|---|---|
| 10 minutes | −19 |
| 30 minutes | −22 |
| 2 hours | −25 |
| 24 hours | −21 |

Synthesis

The procedure is as in Preparation Example 21, with the difference that instead of sodium tetrafluoroborate, 7.0 g (20 mmol) of sodium tetraphenylborate, dissolved in ml of water, are used.

Yield: 7.6 g (84.6% of theory) of the compound 16.1b, white powder

Molecular weight: 998

Melting point: 292° C. (decomposition)

$^1$H—NMR (in DMSO-$d_6$): 3.19 (singlet, 12 methyl-H), 3.46 (singlet, 8 piperazino-H), 3.82 (singlet, 8 piperazino-H), 7.03 (multiplet, 40 phenyl-H), 7.55 (singlet, 4 phenylene-H) ppm.

We claim:

1. Method of using biscationic acid and acid imide derivatives of the general formula (I) and/or (II) and/or (III)

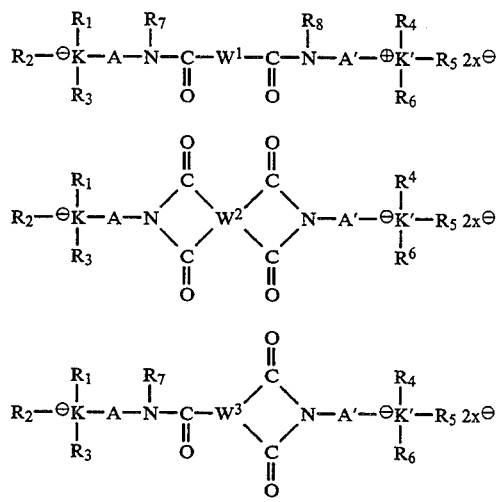

in which $R_1$ to $R_8$ independently of one another are each a hydrogen atom or a hydrocarbon radical, which can be interrupted by hetero atoms, and in which the radicals $R_1$ and $R_2$, or $R_4$ and $R_5$, independently of one another, incorporating K or K', can be closed together to form a ring system, and in the case where $R_1$ or $R_2$, or $R_4$ or $R_5$ in this connection form a double bond to K or K', $R_3$ and $R_6$ have no meaning, and/or in which one of the radicals $R_1$, $R_2$ or $R_3$ can be closed together with $R_7$, or one of the radicals $R_4$, $R_5$ or $R_6$ can be closed together with $R_8$ to form an aliphatic bridge of 2 to 5 carbon atoms, and in which A and A' and $W^1$, $W^2$ and $W^3$ independently of one another are each a bridge member based on a hydrocarbon, which can be interrupted by hetero atoms, and in which $W^1$ is a divalent, $W^2$ a tetravalent and $W^3$ a trivalent bridge member, and in which $W^1$ can also be a direct bond and K and K' independently of one another can each be a nitrogen, phosphorus, arsenic or antimony atom, and the anion $X^\ominus$ is the stoichiometric equivalent of one or more organic or inorganic, mixed or non-mixed anions, it also being possible for the compound to be present as a mixed crystal with various cations of the general formulae (I) to (III), individually or in combination comprising using said derivative as charge controllers for toners and developers which are used for electrophotographic copying or multicopying of originals and for printing electronically, optically or magnetically stored data or in color proofing, or as charge controllers for powders and powder paints.

2. Method of using biscationic acid amide and acid imide derivatives according to claim 1, wherein the formulae (I) to (III) mentioned in claim 1, K and K' are each a nitrogen atom.

3. Method of using biscationic acid amide and acid imide derivatives according to claim 1 wherein, in the formula (I) to (III) mentioned in claim 1, $R_1$ to $R_8$ independently of one another are hydrogen atoms, straight-chain or branched saturated or unsaturated alkyl groups having 1 to 30 carbon atoms, polyoxyalkylene groups of the general formula -(alkylene($C_1$-$C_5$)—O)$_n$R, in which R is a hydrogen atom or an alkyl($C_1$-$C_4$) group or an acyl group and n is a number from 1 to 10, a mono- or polynuclear cycloaliphatic radical having 5 to 12 carbon atoms or a mono- or polynuclear aromatic or an araliphatic radical, and in which such aliphatic, cycloaliphatic, araliphatic and aromatic radicals can be substituted by carboxylic and/or sulfonic acid groups, or salts, amides or esters thereof, hydroxyl, alkyl($C_1$-$C_4$) or alkoxy ($C_1$-$C_4$) groups or primary, secondary or tertiary amino groups, and by fluorine, chlorine or bromine atoms, and in which the aliphatic, cycloaliphatic, araliphatic or aromatic ring systems mentioned can contain one or more hetero atoms, and in which $R_1$ and $R_3$, or $R_4$ and $R_5$ independently of one another can be closed together, incorporating K or K', to form a saturated or aromatic or non-aromatic 5- to 7-membered ring system, which can contain further hetero atoms and can be substituted and/or modified by condensation of or bridging to further ring systems, and in which, in the case where $R_1$ or $R_2$, or $R_4$ or $R_5$ form a double bond to K or K', $R_3$ and $R_6$ have no meaning.

4. Method of using the biscationic acid amide and acid imide derivatives according to claim 1, wherein, in the formulae (I) to (III) mentioned in claim 1, A and A' independently of one another are each a straight-chain or branched, saturated or unsaturated, aliphatic bridge member having 1 to 30 carbon atoms, a mono- or polynuclear cycloaliphatic bridge member or a mono- or polynuclear aromatic bridge member or araliphatic bridge member, in which the aliphatic, cycloaliphatic, araliphatic and aromatic bridge members can be substituted by hydroxyl, carboxylic and/or sulfonic acid groups, or salts, amides or esters thereof, alkyl($C_1$-$C_4$) or alkoxy($C_1$-$C_4$) groups, or primary, secondary or tertiary amino groups, and by fluorine, chlorine or bromine atoms, and in which the aliphatic, cycloaliphatic, aromatic and araliphatic ring systems mentioned can contain one or more nitrogen and/or oxygen and/or sulfur atoms.

5. Method of using biscationic acid amide and acid imide derivatives according to claim 1 wherein $W^1$, in the formulae (I) to (III) mentioned in claim 1, as a divalent bridge member is a straight-chain or branched, saturated or unsaturated aliphatic bridge member having 1 to 30 carbon atoms, a polyoxyalkylene member of the general formula $-CH_2-O-$ (alkylene($C_1$-$C_5$)$-O)_mCH_2-$, in which m is a number from 0 to 10, a mono- or polynuclear cycloaliphatic bridge member having 5 to 12 carbon atoms, a mono- or polynuclear aromatic bridge member, or an araliphatic bridge member, wherein the aliphatic, cycloaliphatic, araliphatic and aromatic bridge members can be substituted by carboxylic and/or sulfonic acid groups, or salts, amides or esters thereof, hydroxyl, alkyl($C_1$-$C_4$) or alkoxy($C_1$-$C_4$) groups or primary, secondary or tertiary amino groups, and by fluorine, chlorine or bromine atoms, and in which the aliphatic intermediate members and the cycloaliphatic, the araliphatic and the aromatic ring systems can contain one or more nitrogen and/or oxygen and/or sulfur atoms, and in which $W^1$ can also be a direct bond, $W^2$ as a tetravalent bridge member is a straight-chain or branched, saturated or unsaturated aliphatic bridge member having 2 to 30 carbon atoms, a mono- or polynuclear aromatic, cycloaliphatic bridge member having 5 to 12 carbon atoms or an araliphatic bridge member, and in which the aliphatic, cycloaliphatic, araliphatic and aromatic bridge members can be substituted by carboxylic and/or sulfonic acid groups, or salts, amides or esters thereof, hydroxyl, alkyl($C_1$-$C_4$) or alkoxy($C_1$-$C_4$) groups or primary, secondary or tertiary amino groups, and by fluorine, chlorine or bromine atoms, and in which the aliphatic bridge members and the cycloaliphatic, the araliphatic and the aromatic ring systems can contain one or more nitrogen and/or oxygen and/or sulfur atoms, and $W^3$ as a trivalent bridge member is a straight-chain or branched, saturated or unsaturated aliphatic bridge member having 2 to 30 carbon atoms, a mono- or polynuclear cycloaliphatic bridge member having 5 to 12 carbon atoms, a mono- or polynuclear aromatic bridge member or an araliphatic bridge member, in which the aliphatic, araliphatic and aromatic bridge members can be substituted by carboxylic and/or sulfonic acid groups, or salts, amides or esters thereof, hydroxyl, alkyl($C_1$-$C_4$) or alkoxy($C_1$-$C_4$) groups or primary, secondary or tertiary amine groups, and by fluorine, chlorine or bromine atoms, and in which the aliphatic bridge members and the cycloaliphatic, the araliphatic and the aromatic ring systems can contain one or more nitrogen and/or oxygen and/or sulfur atoms.

6. Method of using biscationic acid amide and imide derivatives according to claim 1 wherein, in the formulae (I) to (III) mentioned in claim 1, the anion $X^\ominus$ is a halide, $PF_6^\ominus$, $SO_4^{2-}$, $HSO_4^\ominus$, phosphate, $NO_3^\ominus$, cyanate, thiocyanate, $BF_4^\ominus$, $B(aryl)_4^\ominus$, phenolate, nitrophenolate, zinc tetracyanate, zinc tetrathiocyanate, $CH_3OSO_3^\ominus$, $C_2H_5OSO_3^\ominus$ or saturated or unsaturated, aliphatic or aromatic carboxylate or sulfonate, or a tungstate, molybdate or hetero polyacid anion, it also being possible for these anions to be present in mixed form.

7. Method of using biscationic acid amide and acid imide derivatives according to claim wherein in the formulae (I) to (III) mentioned in claim 1, K and K' are each a nitrogen atom, $R_1$ to $R_6$ either independently of one another are each a hydrogen atom or a ($C_1$-$C_4$)-alkyl group, or $R_1$ and $R_2$, or $R_4$ and $R_5$ independently of one another can be closed together, incorporating K or K', to form a saturated or unsaturated 5- or 6-membered heterocyclic ring system having one or two nitrogen atoms as the hetero constituent, in which case $R_3$ and $R_6$ independently of one another are each a hydrogen atom or a ($C_1$-$C_4$)-alkyl group, or in the case where $R_1$ or $R_2$, or $R_4$ or $R_5$ form a double bond to K or K' in this connection, $R_3$ and $R_6$ have no meaning, and $R_7$ and $R_8$ are a hydrogen atom, and A and A' independently of one another is each a $(CH_2)_p$ bridge member, where p is 1 to 4, or a phenylene, naphthylene or

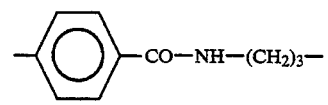

bridge member, $W^1$ a phenylene, naphthylene, cyclohexylene or a $(CH_2)_q$ bridge member, where q is 1 to 12, or a $(CH_2-O(CH_2-CH_2-O)_r-CH_2-$ bridge member, where r is 1-4, $W^2$ a phenylene or naphthylene bridge member, in which the carboxyl groups required for imide formation are in each case in the ortho-position relative to one another in the case of phenylene and in the ortho- and/or periposition relative to one another in the case of naphthylene, or an ethylenediaminetetramethylene bridge member, and $W^3$ is a phenylene or naphthylene bridge member, and the anion $X^\ominus$ is a $B(aryl)_4^\ominus$, $BF_4^\ominus$, $PF_6^\ominus$, $SCN^\ominus$ or $CH_5SO_4^\ominus$.

8. Method of using biscationic acid amide and acid imide derivatives according to claim 1 wherein these derivatives are employed individually or in combination in a concentration of about 0.01 to about 30 percent by weight.

9. Method according to claim 1, wherein at least one of said derivatives is introduced as a constituent of coatings of carriers which are employed in developers for electrophotographic copying or multicopying of originals and for printing electronically, optically or magnetically stored data or in color printing. said derivatives, individually or in combination, is introduced as a charge-improving agent in powders and paints for surface coating of objects of metal, wood, plastic, glass, ceramic, concrete, textile material, paper or rubber.

10. Method according to claim 1, wherein at least one of said derivatives, individually or in combination, is introduced as a charge-improving agent in powders and paints for surface coating of objects of metal, wood, plastic, glass, ceramic, concrete, textile material, paper or rubber.

* * * * *